United States Patent
Narasimhan

(10) Patent No.: US 9,820,696 B1
(45) Date of Patent: Nov. 21, 2017

(54) CUFFLESS BLOOD PRESSURE MEASUREMENT USING HANDHELD DEVICE

(71) Applicant: Ravi Narasimhan, Sunnyvale, CA (US)

(72) Inventor: Ravi Narasimhan, Sunnyvale, CA (US)

( * ) Notice: Subject to any disclaimer, the term of this patent is extended or adjusted under 35 U.S.C. 154(b) by 483 days.

(21) Appl. No.: 14/517,559

(22) Filed: Oct. 17, 2014

Related U.S. Application Data

(60) Provisional application No. 61/893,263, filed on Oct. 20, 2013.

(51) Int. Cl.
  *A61B 5/02* (2006.01)
  *A61B 5/00* (2006.01)
  *A61B 5/021* (2006.01)
  *A61B 7/04* (2006.01)

(52) U.S. Cl.
  CPC .......... *A61B 5/6898* (2013.01); *A61B 5/0077* (2013.01); *A61B 5/02125* (2013.01); *A61B 5/7214* (2013.01); *A61B 5/7278* (2013.01); *A61B 7/045* (2013.01); *A61B 2576/00* (2013.01)

(58) Field of Classification Search
  CPC ................. A61B 7/04; A61B 5/0205
  USPC ....................................................... 600/528
  See application file for complete search history.

(56) References Cited

U.S. PATENT DOCUMENTS

2015/0073239 A1\* 3/2015 Pei ....................... A61B 5/6898
600/324

\* cited by examiner

*Primary Examiner* — Amanda Patton
*Assistant Examiner* — Philip C Edwards
(74) *Attorney, Agent, or Firm* — Young Basile Hanlon & MacFarlane, P.C.

(57) ABSTRACT

A method and system for determining blood pressure are disclosed. The method comprises determining a plurality of heart sounds using a microphone of a handheld device and determining a pulse wave using a camera of the handheld device, wherein the plurality of heart sounds and the pulse wave are utilized to determine the blood pressure. The system includes a processor, a memory device coupled to the processor, and an application coupled to the memory device. The system further comprises a microphone coupled to the processor, wherein the microphone is utilized to determine a plurality of heart sounds and a camera coupled to the processor, wherein the camera is utilized to determine a pulse wave, further wherein the application, when executed by the processor, causes the processor to determine the blood pressure using the plurality of heart sounds and the pulse wave.

6 Claims, 7 Drawing Sheets

CUFFLESS BLOOD PRESSURE MEASUREMENT USING HANDHELD DEVICE

CROSS-REFERENCE TO RELATED APPLICATION

This application claims benefit under 35 USC 119(e) of U.S. Provisional Patent Application No. 61/893,263, filed on Oct. 20, 2013, entitled "CUFFLESS BLOOD PRESSURE MEASUREMENT USING A SMARTPHONE OR HANDHELD DEVICE," which is incorporated herein by reference in its entirety.

FIELD OF THE INVENTION

The present invention relates to handheld devices including but not limited to smartphones, and more particularly, to measuring blood pressure using a handheld device.

BACKGROUND

Hypertension (or high blood pressure) is a large and growing health issue as millions of adults suffer from hypertension which contributes to numerous deaths. In addition, the accurate measurement of a person's blood pressure is important to managing the overall health of the person. Conventionally, blood pressure can be measured using office-based, ambulatory-based, and home-based devices. These conventional devices suffer from a variety of issues including but not limited to white-coat hypertension, uncomfortable cuff squeezes several times per day, and irregular patient compliance. Therefore, there is a strong need for a solution that overcomes the aforementioned issues. The present invention addresses such a need.

SUMMARY OF THE INVENTION

A method and system for determining blood pressure are disclosed. In a first aspect, the method comprises determining a plurality of heart sounds using a microphone of a handheld device and determining a pulse wave using a camera of the handheld device, wherein the plurality of heart sounds and the pulse wave are utilized to determine the blood pressure.

In a second aspect, the system includes a processor, a memory device coupled to the processor, and an application coupled to the memory device. The system further comprises a microphone coupled to the processor, wherein the microphone is utilized to determine a plurality of heart sounds and a camera coupled to the processor, wherein the camera is utilized to determine a pulse wave, further wherein the application, when executed by the processor, causes the processor to determine the blood pressure using the plurality of heart sounds and the pulse wave.

BRIEF DESCRIPTION OF THE DRAWINGS

The accompanying figures illustrate several embodiments of the invention and, together with the description, serve to explain the principles of the invention. One of ordinary skill in the art readily recognizes that the embodiments illustrated in the figures are merely exemplary, and are not intended to limit the scope of the present invention.

DETAILED DESCRIPTION

Figure 1:
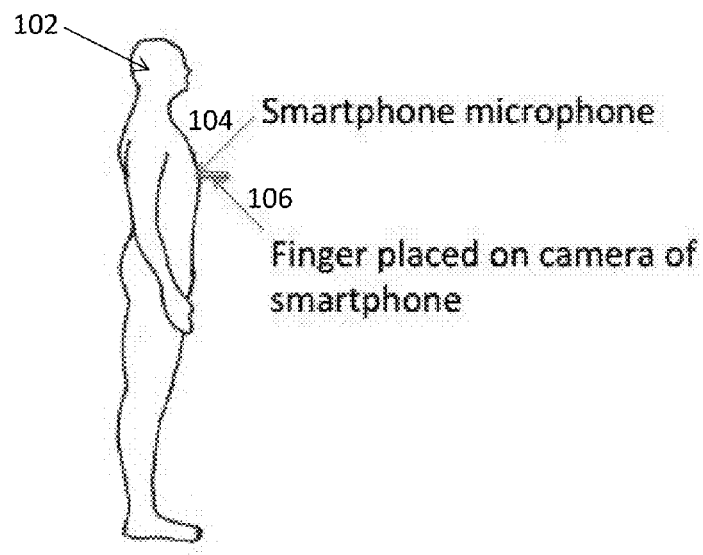
FIG. 1 illustrates a diagram for determining blood pressure using a cuffless handheld device in accordance with an embodiment.

The present invention relates to handheld devices including but not limited to smartphones, and more particularly, to measuring blood pressure using a handheld device. The following description is presented to enable one of ordinary skill in the art to make and use the invention and is provided in the context of a patent application and its requirements. Various modifications to the preferred embodiment and the generic principles and features described herein will be readily apparent to those skilled in the art. Thus, the present invention is not intended to be limited to the embodiments shown but is to be accorded the widest scope consistent with the principles and features described herein.

Hypertension (or high blood pressure) is a serious and chronic health condition in which the blood pressure in the arteries is elevated. Blood pressure is summarized by two measurements, systolic and diastolic, which depend on whether the heart muscle is contracting (systole) or relaxed between beats (diastole). A person's blood pressure can be measured in the office using an auscultatory cuff pump that is a gold standard but this method suffers from white coat hypertension and infrequent access. A person's blood pressure can be measured via ambulatory care which results in several readings over a 24 hour time period but this method suffers from uncomfortable cuff squeezes that occur several times during the day and night. A person's blood pressure can also be measured at home to control hypertension in a comfortable setting but this method suffers from irregular patient compliance and cumbersome medical equipment.

Individuals do not comply with regular home blood pressure monitoring because they: are uncomfortable with an inflatable device, do not want to deal with bulky and expensive equipment, do not have simple, low-cost options to share historical measurements with their physicians, and forget to take measurements. A method and system in accordance with the present invention includes a handheld device (e.g. smartphone) and software platform (application or "App") that provides blood pressure measurements that are comfortable, convenient, low-cost, patient-centric, and digitally and wirelessly connected. The method and system in accordance with the present invention increases patient compliance with blood pressure measurements.

The method and system in accordance with the present invention provides cuffless blood pressure measurement using a handheld device (e.g. smartphone). The method and system is cuffless to provide comfort, does not require any additional equipment beyond the ubiquitous smartphone to provide convenience, includes a software platform/application that costs much less than any blood pressure monitoring equipment to provide a low-cost solution, includes the software platform that can link to other favorite applications with blood pressure measurement reminders to provide a patient-centric solution that increases compliance, and can send measurements easily (e.g. via WiFi, Bluetooth or cellular networks) to provide a connective solution.

In one embodiment, the software platform (or App) utilizes a microphone device and a camera device of the handheld device (e.g. smartphone) to track the blood pressure measurements of the user. In this embodiment, the software platform utilizes only a single handheld/smartphone device to perform cuffless blood pressure measurements of the user and does not require a combination of multiple smartphone and/or external microphone devices to perform the blood pressure measurements. One of ordinary skill in the art readily recognizes that the user can utilize a variety of handheld devices including but not limited to smartphone devices and that would be with the scope of the present invention.

To describe the features of the present invention in more detail, refer now to the following description in conjunction with the accompanying Figures.

The method and system in accordance with the present invention enables a user of a handheld device (including but not limited to a smartphone) that includes an integrated/downloadable software platform (application) to take cuffless blood pressure measurements. In one embodiment, the user holds the smartphone with an internal microphone and places the internal microphone on the user's chest and the microphone is utilized to measure a plurality of phonocardiogram (PCG) heart sounds (associated with a PCG signal) at varying time points (e.g. first heart sound at S1, second heart sound at S2, etc.). In healthy individuals, there are usually only two heart sounds S1 and S2 that repeat with each heartbeat. However, in some instances, there are other heart sounds for each heartbeat (e.g., S3 and S4) that may indicate a heart condition. Alternatively, in another embodiment, the user holds the smartphone on the user's chest near the diaphragm and an external microphone is utilized to measure the PCG heart sounds.

While measuring the PCG signal and the heart sounds, the user places one of their fingers under the camera and the camera is utilized to measure and determine photoplethysmogram (PPG) pulse waves. The negative peak of the PPG signal or its derivative is identified as the pulse wave by the software platform of the smartphone as being when the user's finger is most red due to increased blood flow. Therefore, the user utilizes both the microphone device and the camera device of the smartphone to measure the PCG and PPG signals. FIG. 1 illustrates a diagram 100 for determining blood pressure using a cuffless handheld device (e.g. smartphone). The diagram 100 includes a user 102, a smartphone microphone 104 that is placed on the chest of the user 102 to detect an audio signal that is filtered to determine the PCG signal and the heart sounds are then determined from the PCG signal, and a smartphone camera 106 where the user can place their finger to measure the PPG signal to determine the pulse wave.

After determining the pulse wave as a negative peak of the PPG signal (or its derivative), the software platform is utilized to determine the user's ejection time (ET) as a time delay between the first heart sound (S1) and the second heart sound (S2) that are determined by the software platform from the PCG signal that is measured by the microphone. After measuring the ejection time, the software platform is utilized to determine a vascular transit time (VTT) as a time delay between the first heart sound (S1) to the pulse wave determined as the negative peak of the PPG signal (or its derivative) that is measured by the camera. For a valid VTT, the negative peak of the PPG signal must lie within a certain time interval (e.g., 100 ms to 300 ms) after the first heart sound (S1). After determining the VTT, the smartphone utilizes the VTT, ET, height, weight, age, and gender to determine the systolic and diastolic blood pressure values of the user.

Although different people typically have different VTT values, changes in VTT are negatively correlated to changes in blood pressure as a shorter VTT correlates to a higher blood pressure (BP) whereas a longer VTT correlates to a lower BP. This correlation enables the smartphone to determine the systolic and diastolic blood pressure values of the user without traditional cuffed devices. In one embodiment, if VTT1 and VTT2 denote the VTT at two time points T1 and T2, respectively, and if SBP1 and SBP2 denote the systolic blood pressure (SBP) at T1 and T2, respectively, then the BP measurements of the user can be determined utilizing the following equation (1): SBP2−SBP1=−Ksv*(VTT2−VTT1), where Ksv>0 is a constant (for example, Ksv=0.4 mmHg/ms). If SBP1 and VTT1 (baseline value of VTT) are measured during a calibration phase at time T1 with a reference blood pressure device, a subsequent value at time T2 for the systolic blood pressure can be determined by measuring a new VTT2 and using the equation above to obtain: SBP2=−Ksv*(VTT2−VTT1)+SBP1.

A similar equation can be used for the diastolic blood pressure (DBP). Therefore, in one embodiment, if VTT1 and VTT2 denote the VTT at two time points T1 and T2, respectively, and if DBP1 and DBP2 denote the diastolic blood pressure (DBP) at T1 and T2, respectively, then the BP measurements can be determined utilizing the following equation (2): DBP2−DBP1=−Kdv*(VTT2−VTT1), where Kdv>0 is a constant (for example, Kdv=0.3 mmHg/ms). If DBP1 and VTT1 (baseline value of VTT) are measured during a calibration phase at time T1 with a reference blood pressure device, a subsequent value at time T2 for the diastolic blood pressure can be determined by measuring a new VTT2 and using the equation above to obtain: DBP2=−Kdv*(VTT2−VTT1)+DBP1.

Once the smartphone device obtains a baseline reading of the VTT and ET values using the microphone, camera, and software platform/application of the smartphone device, and determines the blood pressure (BP) measurements, changes in the VTT and ET values and the BP measurements compared to the baseline or previous values of the user can also be tracked. In one embodiment, the tracking utilizes a color code scheme to display, via the smartphone display screen, changes that are low in green, changes that are medium in yellow, and changes that are high in red. The method and system in accordance with the present invention also provides for patient-centric compliance enhancement features including but not limited to the ability for users to configure favorite apps (e.g. voice, text, email, web, etc.) to be unlocked after taking blood pressure measurements or to enable these favorite apps to provide automatic reminders to take blood pressure measurements.

After the VTT and ET values are determined utilizing the microphone and camera devices and the software platform of the smartphone, the blood pressure (BP) measurements of the user can be absolutely determined and calculated using an individual calibration approach or a statistical regression approach. As aforementioned, the individual calibration approach utilizes the initial baseline measurements of VTT and ET together with a blood pressure reading from a reference device. However, after the initial calibration of the individual calibration approach, subsequent BP measurements can be made without utilizing the reference device using the aforementioned equations (1) and (2). The statistical regression approach utilizes a regression analysis that is based on large data sets (e.g. stored on a cloud network) that have been obtained from several users using similar devices.

Figure 2:
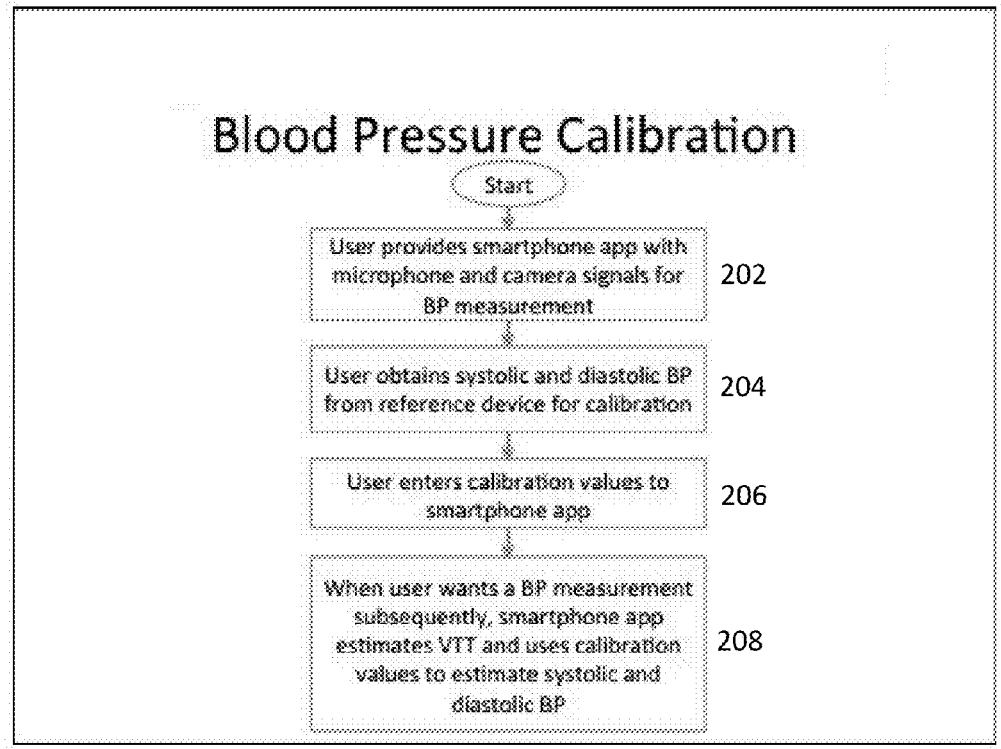
FIG. 2 illustrates a method for determining blood pressure using individual calibration in accordance with an embodiment.

FIG. 2 illustrates a method 200 for determining blood pressure using individual calibration in accordance with an embodiment. The method 200 comprises a smartphone device that includes at least one microphone, at least one camera, and an integrated/downloadable software platform/application (App), wherein a user utilizes the smartphone device to provide microphone and camera signals that are utilized to determine the VTT and ET values for the BP measurement, via step 202. The user then obtains systolic and diastolic blood pressure measurements (calibration values) from a reference device (e.g. the reference device includes but is not limited to any of cuffed, cuffless, home-based, and office-based blood pressure monitoring devices) for calibration, via step 204, and enters the obtained calibration values into the App of the smartphone device, via step 206.

In one embodiment, the calibration is repeated whenever significant physiological changes of the user occur, such as prolonged periods of vasodilation or vasoconstriction, changes in arterial stiffness, and changes in weight. In another embodiment, since the occurrence of significant physiological changes is often unknown, a nominal calibration interval (or predetermined schedule) can be set by the App; for example, the App could be configured such that a calibration is performed once a week or once a month or is repeated after a BP measurement that is outside of the user's typical average range (e.g., a very high or very low BP reading is determined). The predetermined schedule is based upon numerous factors including but not limited to the user's health and needs and clinician input.

When the user wants a subsequent BP measurement, the App determines additional VTT and ET values using a similar process to step 202 (determining VTT and ET values using the microphone and camera devices of the smartphone) and then utilizes the determined VTT and ET values as well as the calibration values to determine the systolic and diastolic BP measurements of the user, via step 208. Additionally, demographic information such as height, weight, gender and age of the user can also be used with the VTT and ET measurements to determine the systolic and diastolic BP measurements. Inclusion of such demographic information could reduce the frequency of calibrations needed for accurate BP measurements. In one embodiment, the smartphone device compares the subsequent BP measurements to the previous BP measurements and the calibration values to track changes and display the results to the user or another user or administrator.

Figure 3:
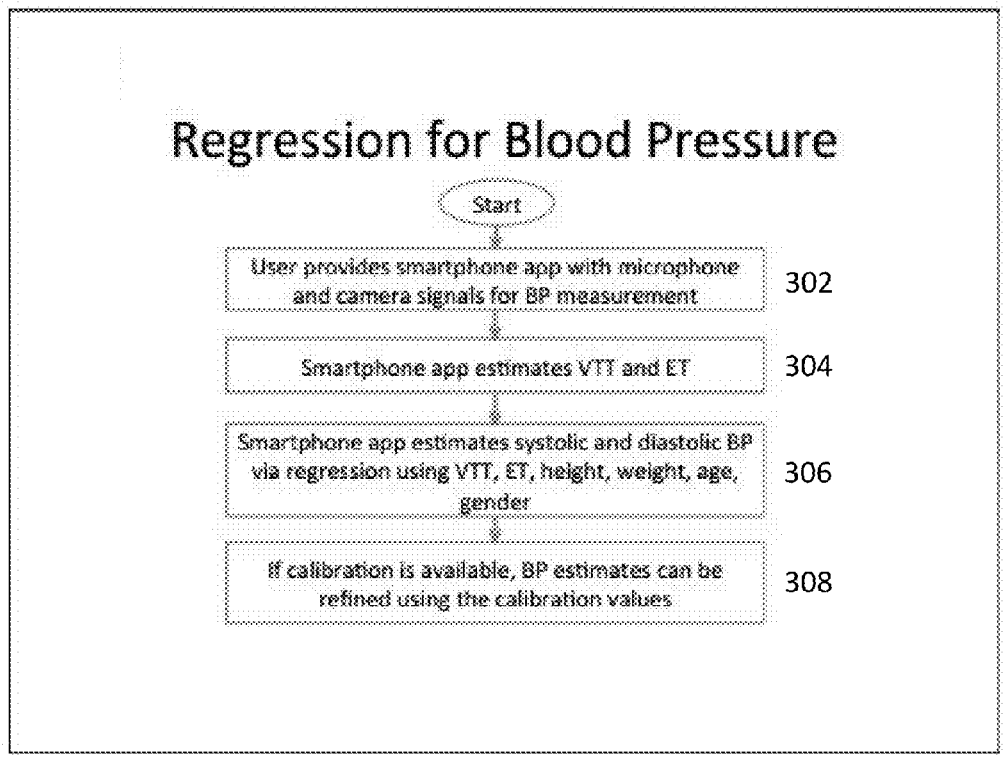
FIG. 3 illustrates a method for determining blood pressure using statistical regression without the need for calibration in accordance with an embodiment.

FIG. 3 illustrates a method 300 for determining blood pressure using statistical regression without the need for calibration in accordance with an embodiment. The method 300 comprises a smartphone device that includes at least one microphone, at least one camera, and an integrated/downloadable software platform/application (App), wherein a user utilizes the smartphone device to provide microphone and camera signals, via step 302, and the smartphone determines the VTT and ET values from the microphone and camera signals for the BP measurement, via step 304. The smartphone determines systolic and diastolic blood pressure (BP) measurements via regression analysis that utilizes VTT, ET, height, weight, age, and gender datasets, via step 306. If calibration is available, the blood pressure measurement determinations from step 304 can be refined using the calibration values in accordance with the method 200, via step 308.

In one embodiment, the datasets contain information from several users with different ranges of systolic and diastolic BP and of each predictor variable (e.g. VTT, ET, height, weight, age, and gender, etc.). The initial datasets can consist of values from clinical studies with reference BP measurements and predictor variables. The datasets can be updated by data from users of the smartphone device and cuffless BP measurement App disclosed by a method and system in accordance with the present invention. For example, each of the user datasets can be uploaded to a central database (e.g. cloud-based) that stores, analyzes, and transmits data back to each of the smartphone devices to enable more accurate BP measurements via the regression analysis. When available, these updated datasets can include BP measurements from reference devices to improve the regression performance.

In one embodiment, the regression analysis performed by step 306 of the method 300 utilizes a linear regression equation in order to account for additional variables beyond VTT. In one embodiment, the linear regression equation for either systolic blood pressure (SBP) or diastolic blood pressure (DBP) can be expressed per the following equation: $y=a_0+a_1*x_1+a_2*x_2+ \ldots +a_p*x_p+e$, where y is either SBP or DBP, $(x_1, \ldots, x_p)$ are predictors, $(a_0, a_1, \ldots, a_p)$ are the coefficients of the linear regression and e is an error term. The coefficients of the linear regression can be determined by a variety of techniques including but not limited to ordinary least squares regression, ridge regression, lasso regression, elastic net regression and principal component regression. The predictors include but are not limited to any of vascular transit time (VTT), ejection time (ET), height, weight, gender, age, and heart rate.

Instantaneous heart rate can be determined by any of (a) the reciprocal of the time difference of the pulse wave of adjacent heartbeats, (b) the reciprocal of the time difference of the S1 heart sound of adjacent heartbeats, (c) the reciprocal of the time difference of the S2 heart sound of adjacent heartbeats, and (d) a combination of (a)-(c). Heart rate can be determined by averaging the instantaneous heart rate over a specified number of beats (for example, 10 beats) or duration (for example, 10 seconds). For a given user, heart rate changes may indicate changes in BP. For example, a heart rate increase for a user may indicate an increase in sympathetic nervous system activity, which may correlate with increased blood pressure. Conversely, a decrease in heart rate may indicate a decrease in sympathetic nervous system activity, which may correlate with decreased blood pressure.

In another embodiment, the regression analysis performed by step 306 of the method 300 utilizes a nonlinear regression equation for SBP or DBP which can be expressed per the following equation: $y=f(x_1, \ldots, x_p)+e$, where $f( )$ is a nonlinear function of the predictors $(x_1, \ldots, x_p)$. Once again, the predictors include but are not limited to any of vascular transit time (VTT), ejection time (ET), height, weight, gender, age, and heart rate.

Figure 4:
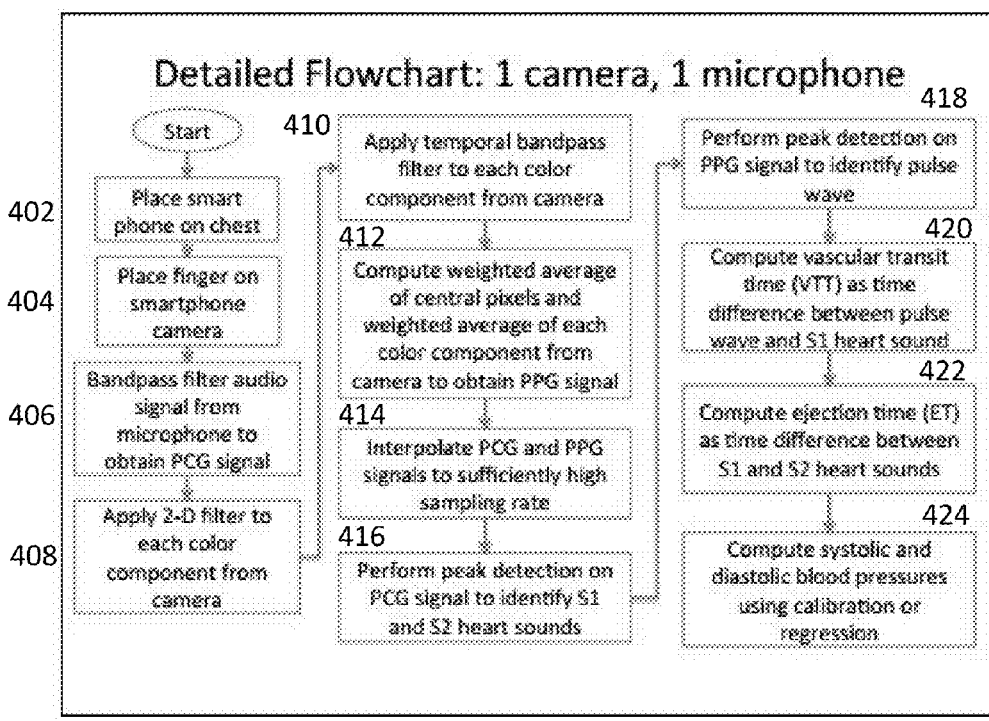
FIG. 4 illustrates a method for determining blood pressure using a handheld device with one camera and one microphone in accordance with an embodiment.

FIG. 4 illustrates a method 400 for determining blood pressure using a handheld device with one camera and one microphone in accordance with an embodiment. The method 400 comprises a user placing a smartphone (or another handheld device with one camera and one microphone) on their chest, via step 402, and placing their finger over the smartphone camera, via step 404. The user places the area of the smartphone that houses the microphone on their chest.

By placing the microphone of the smartphone on the chest, heart-related audio signals are recorded and by placing the user's finger over the camera, pulse-related images are recorded. A bandpass filter (or another type of filter) is utilized to filter the audio signal(s) from the microphone to determine a phonocardiogram (PCG) signal, via step 406. The camera typically provides three color components (red, green and blue) for each pixel. A 2-D filter, for example a 2-D moving average of color component values within a certain region of the image (or another type of filter), is utilized to filter each color component from the camera, via step 408. Then a temporal bandpass filter (or another type of filter) is applied to each color component from the camera, via step 410.

After filtering the audio and visual signals from the microphone and camera devices of the smartphone respectively, a weighted average of each color component of the central pixels from the image is calculated to determine the photoplethysmogram (PPG) signal, via step 412. The PCG signal and the PPG signal are interpolated to a sufficiently high sampling rate (for example, 500 Hz to 10,000 Hz), via step 414. Peak detection (using techniques including but not limited to smoothed slope zero crossings and wavelet decomposition) is performed on the PCG signal to identify at least two heart sounds at different time periods (S1 and S2), via step 416, and negative peak detection is also performed on the PPG signal to identify a pulse wave, via step 418. As aforementioned, a healthy user typically has two heart sounds (S1 and S2) that repeat with each heartbeat. If additional heart sounds are detected (e.g., S3 and S4 indicating a potential heart condition), those additional heart sounds typically repeat with each heartbeat as well.

After identifying the heart sounds and the pulse wave from the PCG signal and the PPG signal respectively, the vascular transit time (VTT) is calculated as a time delay from the first S1 heart sound to the pulse wave, via step 420, and the ejection time (ET) is calculated as a time delay from the S1 to the S2 heart sounds, via step 422. Once the VTT and the ET have been calculated, the systolic and diastolic blood pressures of the user are calculated using either the individual calibration approach of method 200 or the statistical regression approach of method 300, via step 424.

Some smartphone and handheld devices have more than one microphone (e.g. two microphones). In these cases, the software platform/application of the smartphone utilizes the second microphone to cancel noise from the PCG signal. This noise cancellation can be generalized to smartphones with more than two microphones as well (e.g. the additional microphones will all serve to further cancel the noise out).

In addition, some smartphone and handheld devices have more than one camera (e.g. two cameras with one on the front of the device and the other on the back of the device). In these cases, the user can place one finger on the first camera (front or back) and another finger on the second camera (the front or back camera not already covered). The two cameras provide two PPG signals, which are used to determined two VTT values. By taking the difference of the two VTT values, any common mode noise (e.g. pre-ejection period) is cancelled. This enables improved correlation between the difference of the two VTT values and a change in the blood pressure (as aforementioned, there is a negative correlation between changes in VTT and changes in blood pressure). This method can be generalized to smartphones with more than two cameras as well (e.g. the additional cameras will all serve to further cancel the common mode noise out).

Figure 5:
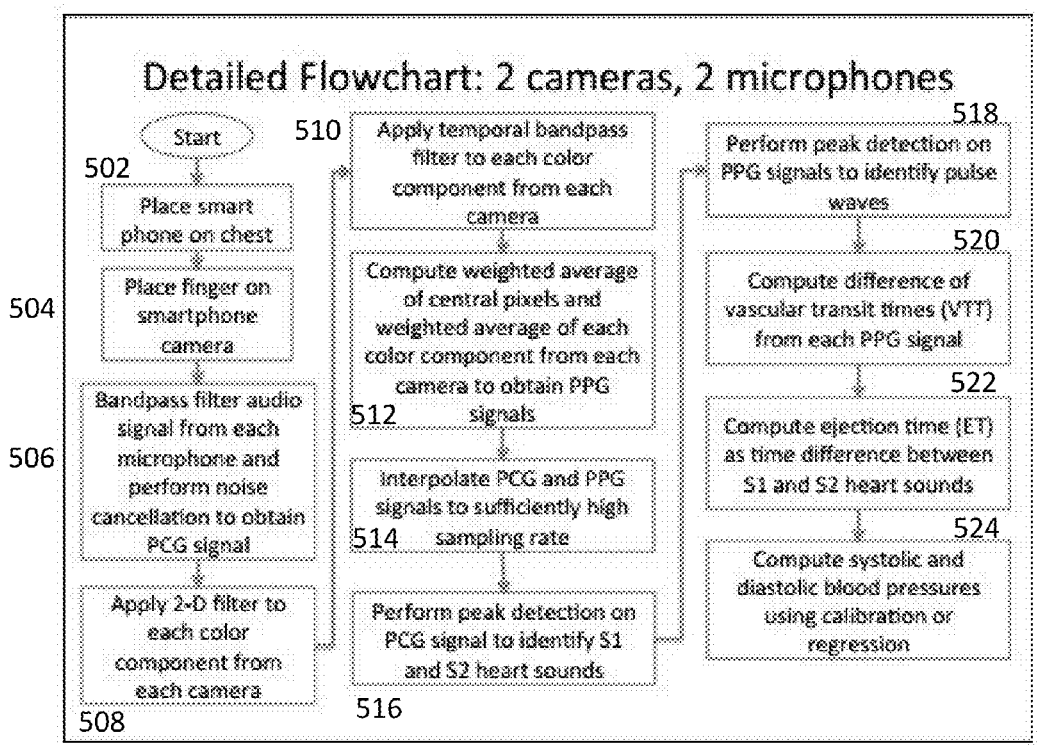
FIG. 5 illustrates a method for determining blood pressure using a handheld device with two cameras and two microphones in accordance with an embodiment.

FIG. 5 illustrates a method 500 for determining blood pressure using a handheld device with two cameras and two microphones in accordance with an embodiment. The method 500 comprises a user placing a smartphone (or another handheld device with two cameras and two microphones) on their chest, via step 502, and placing one finger over each of the two smartphone cameras, via step 504. The user places the area of the smartphone that houses at least one of the two microphones on their chest. The other of the two microphones provides external (non-heart-related) noise cancellation.

By placing the at least one of the two microphones of the smartphone on the chest, heart-related audio sounds are recorded and by placing the user's finger over the each of the two cameras, heart-related images are recorded. A bandpass filter (or another type of filter) is utilized to filter the audio signal(s) from each of the two microphones and perform noise cancellation to determine a phonocardiogram (PCG) signal, via step 506. The camera typically provides three color components (red, green and blue) for each pixel. A 2-D filter, for example a 2-D moving average of color component values within a certain region of the image (or another type of filter), is utilized to filter each color component from each of the two cameras, via step 508, and then a temporal bandpass filter (or another type of filter) is applied to each color component from each of the two cameras, via step 510.

After filtering the audio and visual signals from the two microphone and camera devices of the smartphone respectively, a weighted average of each color component of the central pixels from the image is calculated to determine the photoplethysmogram (PPG) signals, via step 512. The PCG signal and the PPG signals are interpolated to a sufficiently high sampling rate (for example, 500 Hz to 10,000 Hz), via step 514. Peak detection is performed on the PCG signal to identify at least two heart sounds at different time periods (S1 and S2), via step 516, and negative peak detection is also performed on the PPG signals to identify a plurality of pulse waves, via step 518.

After identifying the heart sounds and the plurality of pulse waves from the PCG signal and the PPG signals respectively, each of a plurality of vascular transit times (VTTs) is calculated as a time difference between each pulse wave of each PPG signal and the first S1 heart sound, and the VTTs are subtracted to remove common mode noise, via step 520, and the ejection time (ET) is calculated as a time difference between the S1 and S2 heart sounds, via step 522. Once the VTT difference and the ET have been calculated, the systolic and diastolic blood pressures of the user are calculated using either the individual calibration approach of method 200 or the statistical regression approach of method 300, via step 524.

Once the blood pressures (both systolic and diastolic) of the user are calculated, this data as well as the previously determined data (VTT, ET, heart rate, etc.) and the submitted data (height, weight, age, gender, etc.) are uploaded or transferred to another user, device, or cloud-server via WiFi, Bluetooth, NFC, cellular networks or another connection protocol for storage and analysis. This enables the data to be easily stored, tracked, and viewable by the user's physician or another administrator or health-related personnel. The smartphone device can also set automated and continuous uploads of data so that the blood pressure measurements can be continuously monitored and tracked over varying periods of time.

Figure 6:
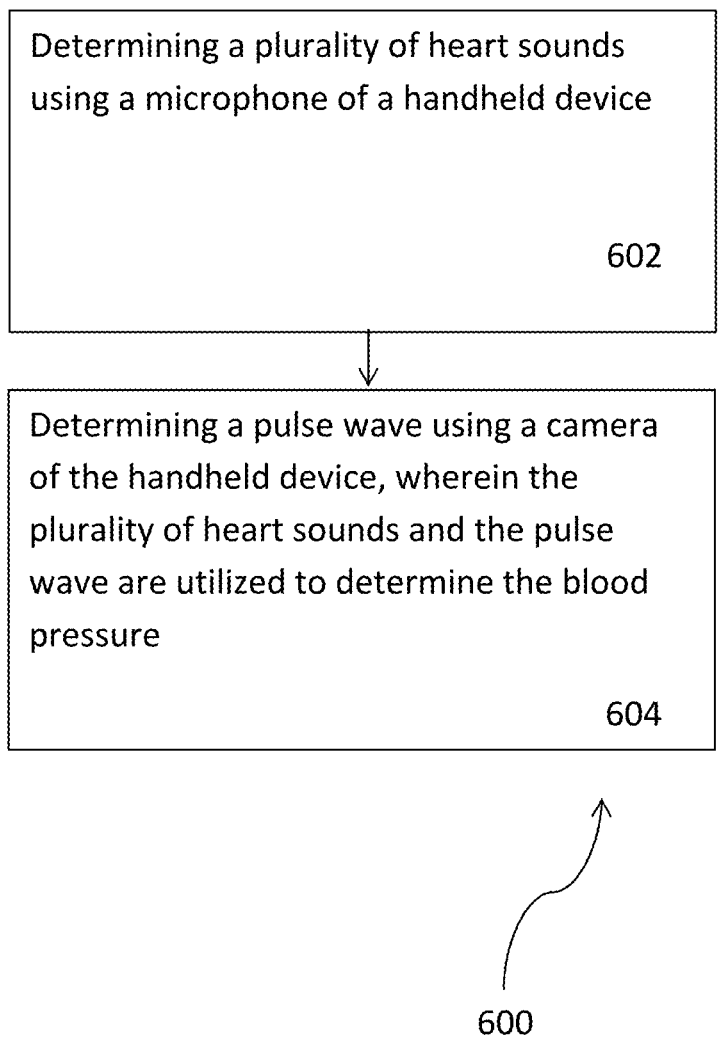
FIG. 6 illustrates a method for determining blood pressure in accordance with an embodiment.

FIG. 6 illustrates a method 600 for determining blood pressure in accordance with an embodiment. The method 600 includes determining a plurality of heart sounds using a microphone of a handheld device, via step 602, and determining a pulse wave using a camera of the handheld device, wherein the plurality of heart sounds and the pulse wave are utilized to determine the blood pressure, via step 604. The plurality of heart sounds is determined by placing the microphone on the chest of a user and the pulse wave is determined by placing a finger of the user over the camera. In another embodiment, the method 600 further comprises determining an ejection time (ET) from the plurality of heart sounds, determining a vascular transit time (VTT) from at least one of the plurality of heart sounds and the pulse wave, and determining a heart rate from any of the plurality of heart sounds and the pulse wave.

The determining the ET step further comprises determining the ET as a time difference between a first and a second heart sound of the plurality of heart sounds. The determining the VTT step further comprises determining the VTT as a time difference between a first heart sound of the plurality of heart sounds and the pulse wave. The determining the heart rate step further comprises determining the heart rate as an average of the reciprocal of a time difference between any of a first heart sound of one heartbeat and a first heart sound of an adjacent heartbeat, a second heart sound of one heartbeat and a second heart sound of an adjacent heartbeat, and a pulse wave of one heartbeat and a pulse wave of an adjacent heartbeat.

In another embodiment, the method 600 further comprises providing user-specific data and performing regression analysis on the user-specific data, the determined ET, the determined VTT, and the determined heart rate to determine the blood pressure by an application of the handheld device. The user-specific data includes but is not limited to any of height, weight, age, and gender. The regression analysis performed by the application of the handheld device includes but is not limited to any of statistical linear regression and statistical non-linear regression.

In another embodiment, the method 600 further comprises providing calibration values to an application of the handheld device using a reference device and utilizing the calibration values, the determined ET, the determined VTT, and the determined heart rate to determine the blood pressure by the application of the handheld device. The reference device includes but is not limited to cuffed or cuffless office or home-based devices.

In another embodiment, the method 600 further comprises filtering an audio signal detected by the microphone to provide a phonocardiogram (PCG) signal and performing peak detection on the PCG signal to determine the plurality of heart sounds, including the first and the second heart sound of the plurality of heart sounds. In addition, the method 600 further comprises filtering color components obtained by the camera, calculating a weighted average of the filtered color components to provide a photoplethysmogram (PPG) signal, and performing peak detection on the PPG signal to determine the pulse wave.

In one embodiment, a system (e.g. handheld device or smartphone) for determining blood pressure in accordance with the steps of the method 600 is disclosed. The system includes a processor, a memory device coupled to the processor, and an application coupled to the memory device. The system further comprises a microphone coupled to the processor, wherein the microphone is utilized to determine a plurality of heart sounds and a camera coupled to the processor, wherein the camera is utilized to determine a pulse wave, further wherein the application, when executed by the processor, causes the processor to determine the blood pressure using the plurality of heart sounds and the pulse wave.

In another embodiment, the system includes at least one other microphone (the system can include more than two microphones) coupled to the processor, wherein the at least one other microphone is utilized to perform noise cancellation and the system also includes at least one other camera (the system can include more than two cameras) coupled to the processor, wherein the at least one other camera is utilized to perform common mode noise cancellation.

Figure 7:
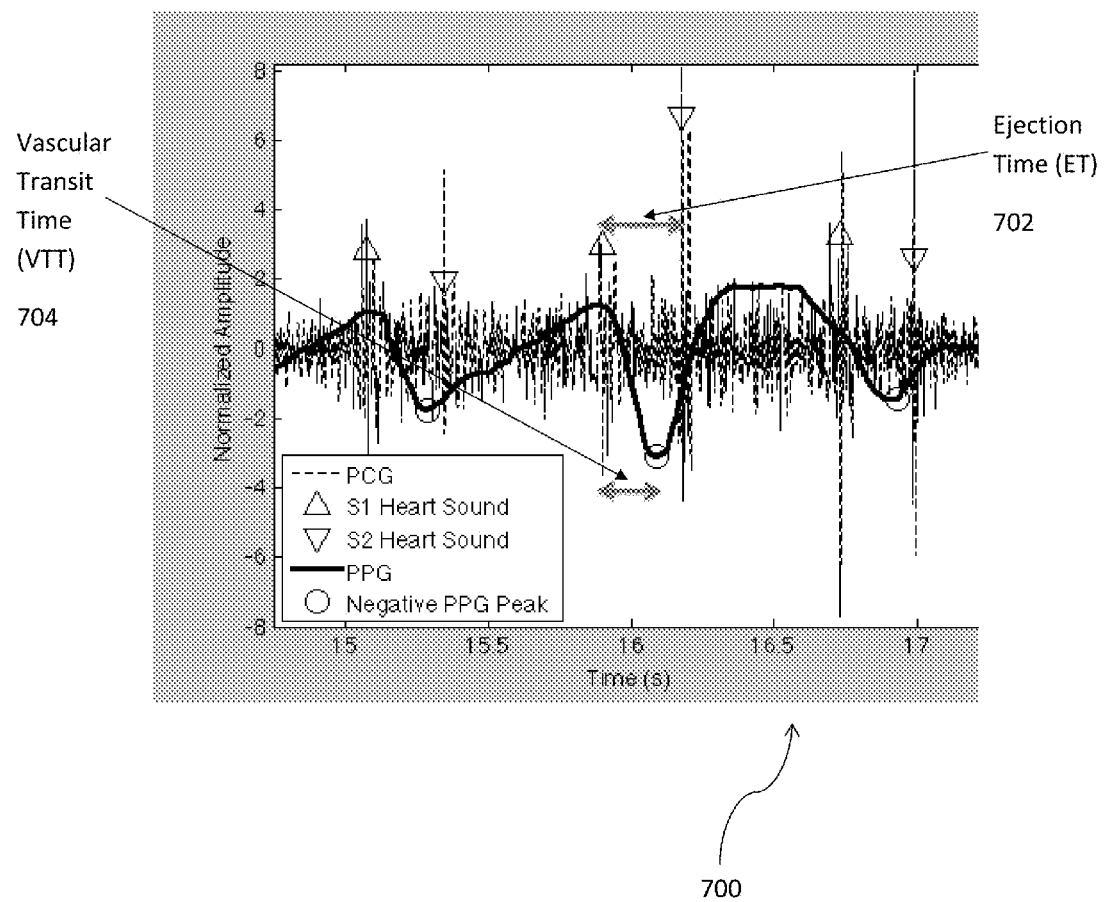
FIG. 7 illustrates a diagram of heart-related measurements measured by a cuffless handheld device in accordance with an embodiment.

FIG. 7 illustrates a diagram 700 of heart-related measurements measured by a cuffless handheld device in accordance with an embodiment. The diagram 700 plots time (in seconds) versus a normalized amplitude of a plurality of heart-related measurements that include a PCG signal, a PPG signal, a plurality of first heart sounds (S1), a plurality of second heart sounds (S2), and a plurality of negative PPG peaks (pulse waves). In addition, the diagram 700 also includes an ejection time (ET) 702 and a vascular transit time (VTT) 704. In diagram 700, for each heartbeat, the first and the second heart sounds S1 and S2 are repeating. Therefore, the microphone detects an audio signal that is filtered into a PCG signal that covers a plurality of heartbeats and thus a plurality of first (S1) and second (S2) heart sounds.

As aforementioned, the ET 702 is calculated as a time delay between a first heart sound (S1) and a second heart sound (S2) that were measured using an audio signal detected by the microphone of the cuffless handheld device; and the VTT 704 is calculated as a time delay between a first heart sound (S1) and a pulse wave (determined as a negative peak of the PPG signal detected by the camera of the cuffless handheld device). Utilizing either the aforementioned individual calibration approach or the statistical regression approach, the blood pressure (BP) systolic and diastolic measurements are calculated using the ET and VTT values.

As above described, a method and system in accordance with the present invention utilizes a handheld device (e.g. smartphone) that includes at least one integrated microphone and at least one integrated camera in conjunction with a software platform/application (App) that is either subsequently downloaded by the user or already preinstalled onto the smartphone device to determine the blood pressure (both systolic and diastolic) of the user. The method and system increase patient compliance with home-based blood pressure monitoring by providing a device that is comfortable, convenient, low-cost, patient-centric, and connected. In addition, by utilizing statistical regression and analyzing large datasets of stored user data related to blood pressure measurements, the method and system determines the blood pressure of the user without utilizing a cuffed blood pressure monitoring device.

A method and system for determining blood pressure has been disclosed. Embodiments described herein can take the form of an entirely hardware implementation, an entirely software implementation, or an implementation containing both hardware and software elements. Embodiments may be implemented in software, which includes, but is not limited to, application software, firmware, resident software, microcode, etc.

The steps described herein may be implemented using any suitable controller or processor, and software application, which may be stored on any suitable storage location or calculator-readable medium. The software application provides instructions that enable the processor to perform the functions described herein.

Furthermore, embodiments may take the form of a calculator program product accessible from a calculator-usable or calculator-readable medium providing program code for use by or in connection with a calculator or any instruction execution system. For the purposes of this description, a calculator-usable or calculator-readable medium can be any apparatus that can contain, store, communicate, propagate, or transport the program for use by or in connection with the instruction execution system, apparatus, or device.

The medium may be an electronic, magnetic, optical, electromagnetic, infrared, semiconductor system (or apparatus or device), or a propagation medium. Examples of a calculator-readable medium include a semiconductor or solid state memory, magnetic tape, a removable calculator diskette, a random access memory (RAM), a read-only memory (ROM), a rigid magnetic disk, and an optical disk. Current examples of optical disks include DVD, compact disk-read-only memory (CD-ROM), and compact disk-read/write (CD-RAN).

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

What is claimed is:

1. A system for determining blood pressure, wherein the system includes a processor, a memory device coupled to the processor, and an application coupled to the memory device, wherein the system further comprises:
    a microphone coupled to the processor, wherein the microphone is utilized to determine a plurality of heart sounds; and
    a camera coupled to the processor, wherein the camera is utilized to determine a pulse wave, further wherein the application, when executed by the processor, causes the processor to:
        determine an ejection time (ET), a vascular transit time (VTT), and a heart rate from any of the plurality of heart sounds and the pulse wave; and
        perform regression analysis on received user-specific data, the ET, the VTT, and the heart rate to determine the blood pressure.

2. The system of claim 1, wherein to determine the ET further comprises to: determine the ET as a time difference between a first and a second heart sound of the plurality of heart sounds.

3. The system of claim 1, wherein to determine the VTT further comprises to:
    determine the VTT as a time difference between a first heart sound of the plurality of heart sounds and the pulse wave.

4. The system of claim 1, wherein to determine the heart rate further comprises to: determine the heart rate as an average of the reciprocal of a time difference between any of a first heart sound of one heartbeat and a first heart sound of an adjacent heartbeat, a second heart sound of one heartbeat and a second heart sound of an adjacent heartbeat, and a pulse wave of one heartbeat and a pulse wave of an adjacent heartbeat.

5. The system of claim 1, wherein the application, when executed by the processor, further causes the processor to:
    utilize calibration values from a reference device, the determined ET, the determined VTT, and the determined heart rate to determine the blood pressure.

6. The system of claim 1, wherein the system further comprises:
    another microphone coupled to the processor, wherein the another microphone is utilized to perform noise cancellation; and
    another camera coupled to the processor, wherein the another camera is utilized to perform common mode noise cancellation.

* * * * *